(12) United States Patent
Koizumi et al.

(10) Patent No.: US 12,109,359 B2
(45) Date of Patent: Oct. 8, 2024

(54) OXYGEN SUPPLY DEVICE AND METHOD FOR CONTROLLING SAME

(71) Applicant: Teijin Pharma Limited, Tokyo (JP)

(72) Inventors: Ryo Koizumi, Tokyo (JP); Sadayoshi Matsumoto, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 1412 days.

(21) Appl. No.: 16/498,627

(22) PCT Filed: Mar. 19, 2018

(86) PCT No.: PCT/JP2018/010818
§ 371 (c)(1),
(2) Date: Sep. 27, 2019

(87) PCT Pub. No.: WO2018/180706
PCT Pub. Date: Oct. 4, 2018

(65) Prior Publication Data
US 2020/0094007 A1 Mar. 26, 2020

(30) Foreign Application Priority Data
Mar. 31, 2017 (JP) .................................. 2017-069845

(51) Int. Cl.
*A61M 16/00* (2006.01)
*A61B 5/08* (2006.01)
*A61B 5/1455* (2006.01)

(52) U.S. Cl.
CPC ......... *A61M 16/026* (2017.08); *A61B 5/0816* (2013.01); *A61B 5/14551* (2013.01);
(Continued)

(58) Field of Classification Search
CPC .. A61M 16/00; A61M 16/026; A61M 16/101; A61M 16/0051; A61M 16/0003;
(Continued)

(56) References Cited

U.S. PATENT DOCUMENTS

2008/0295839 A1* 12/2008 Habashi ............ A61M 16/0051
128/204.22
2014/0007870 A1 1/2014 Franberg et al.
(Continued)

FOREIGN PATENT DOCUMENTS

CN 105120751 A 12/2015
CN 105828888 A 8/2016
(Continued)

OTHER PUBLICATIONS

Communication, dated Jun. 11, 2021, issued by The State Intellectual Property Office of P.R. of China in Application No. 201880022213.0.
(Continued)

*Primary Examiner* — Samchuan C Yao
*Assistant Examiner* — Nathan M Le
(74) *Attorney, Agent, or Firm* — Sughrue Mion, PLLC

(57) ABSTRACT

The oxygen supply device supplying a user with an oxygen gas for inhalation comprises: a first sensor unit acquiring information on percutaneous arterial oxygen saturation (SpO2) of the user, a second sensor unit acquiring information on respiratory frequency per minute (BPM), and a control unit. Under the condition where the SpO2 level acquired by the first sensor unit is equal to or larger than the predetermined first threshold and the BPM value acquired by second sensor unit is equal to or larger than the predetermined second threshold, the control unit regards the condition as a possible sign of CO2 narcosis that exhibits an increase in PaCO2 level, and thus judges the condition as an abnormal sign. Then the control unit executes controls such as stopping supply of the oxygen gas to the user, and the like.

15 Claims, 3 Drawing Sheets

(52) U.S. Cl.
CPC ............... *A61M 2202/0007* (2013.01); *A61M 2202/0208* (2013.01); *A61M 2205/18* (2013.01); *A61M 2230/42* (2013.01)

(58) Field of Classification Search
CPC ............ A61M 16/10; A61M 2230/202; A61B 5/0816; A61B 5/04551; A61B 5/08; A61B 5/145
See application file for complete search history.

(56) References Cited

U.S. PATENT DOCUMENTS

| | | | |
|---|---|---|---|
| 2016/0015296 A1* | 1/2016 | Garaycochea | A61M 16/0688 128/207.18 |
| 2016/0029973 A1* | 2/2016 | Kahlman | A61B 5/14539 600/301 |
| 2016/0058346 A1* | 3/2016 | Heinonen | A61B 5/14542 600/301 |
| 2016/0095994 A1* | 4/2016 | Currin | A61M 16/20 128/203.14 |
| 2018/0153440 A1* | 6/2018 | Lee | A61B 5/7278 |

FOREIGN PATENT DOCUMENTS

| | | |
|---|---|---|
| JP | 2001-309981 A | 11/2001 |
| JP | 2003-062075 A | 3/2003 |
| JP | 2003-126256 A | 5/2003 |
| JP | 2008-067941 A | 3/2008 |
| JP | 2013-208217 A | 10/2013 |
| JP | 2014-064772 A | 4/2014 |

OTHER PUBLICATIONS

Communication, dated Feb. 25, 2020, issued by the European Patent Office in European Application No. 18775445.2.
International Search Report for PCT/JP2018/010818 dated Jun. 26, 2018 [PCT/ISA/210].

* cited by examiner

[Fig. 1]
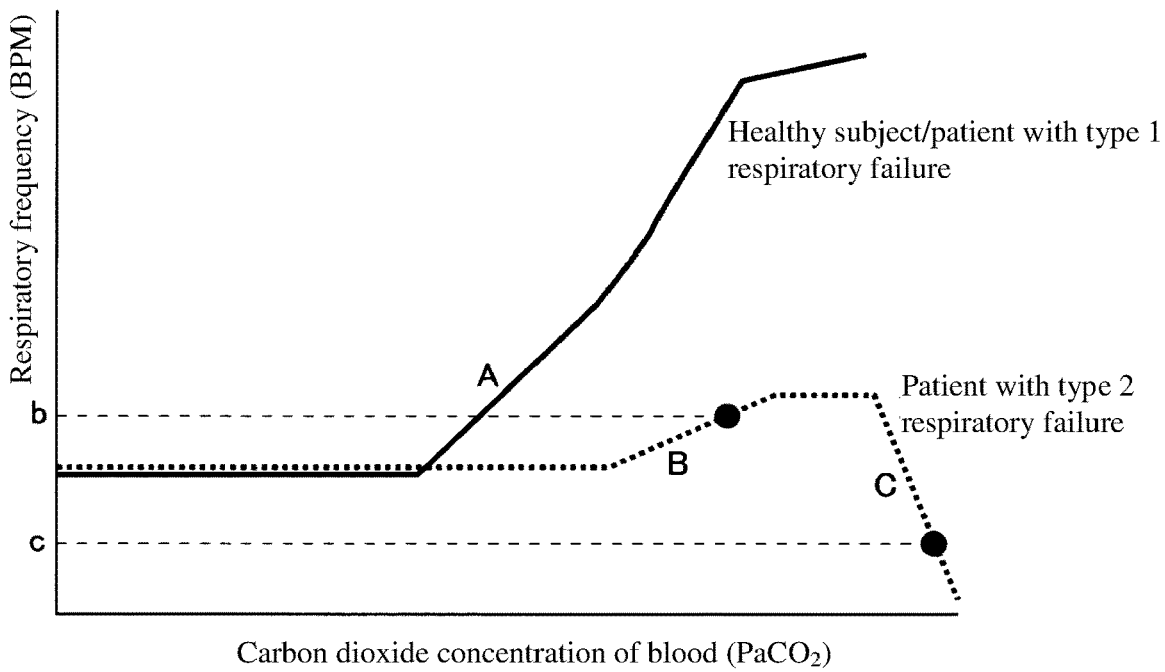
[Fig. 2]
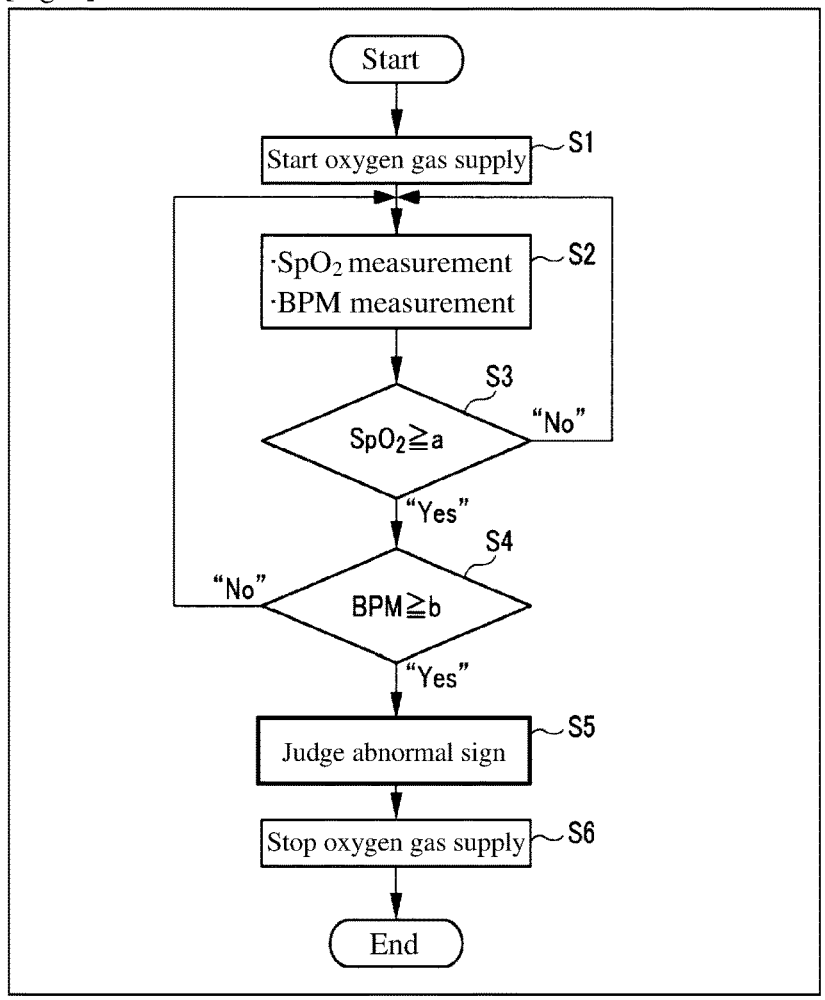

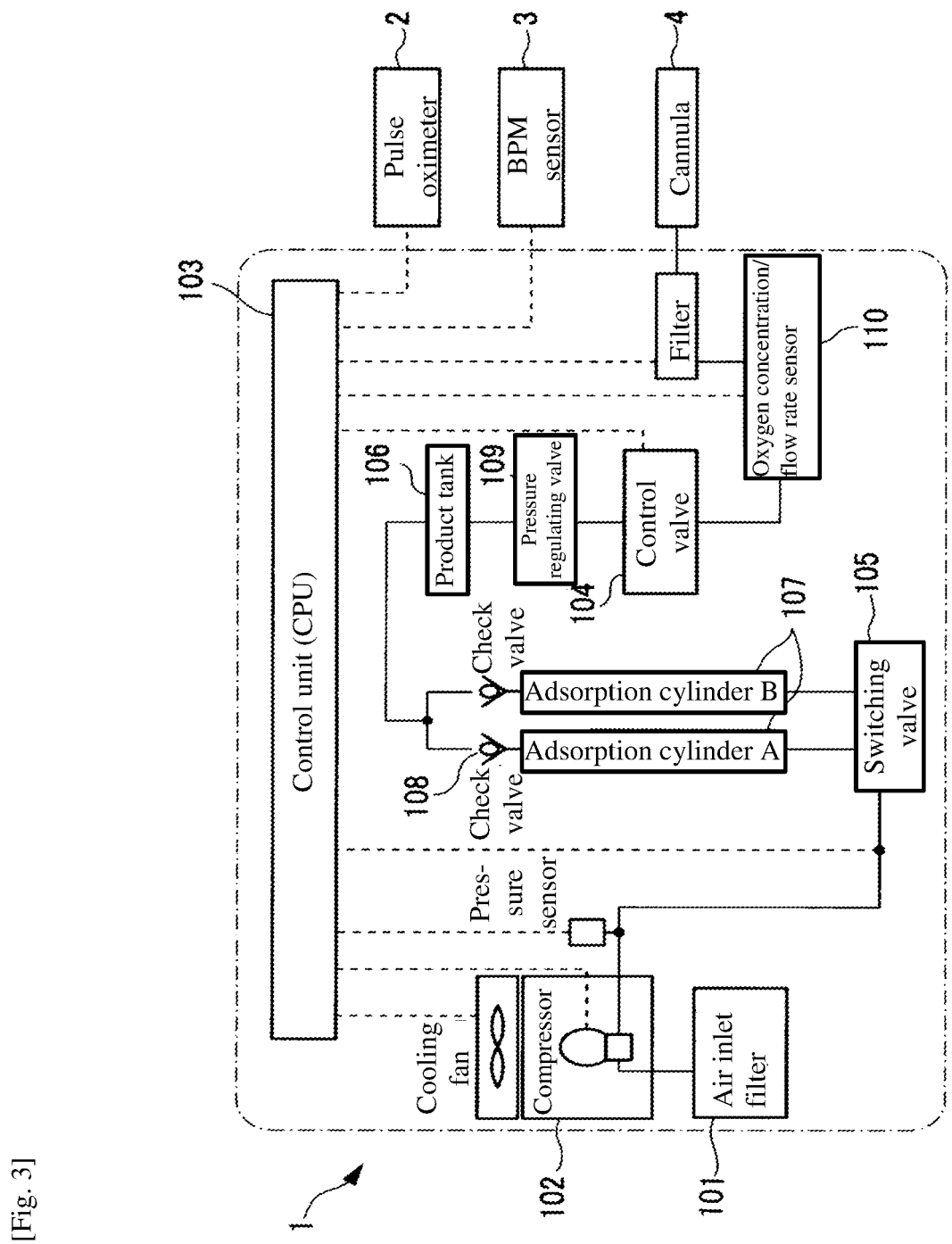
[Fig. 3]

[Fig. 4]
(a) Fig. 4a
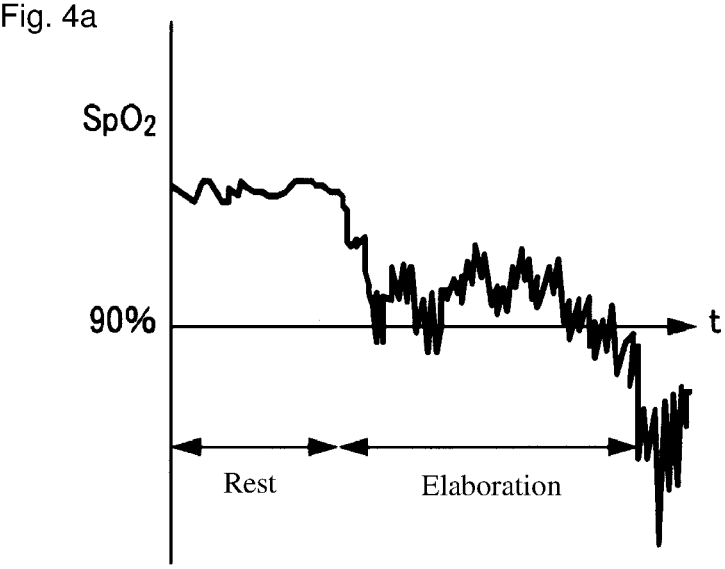
(b) Fig. 4b
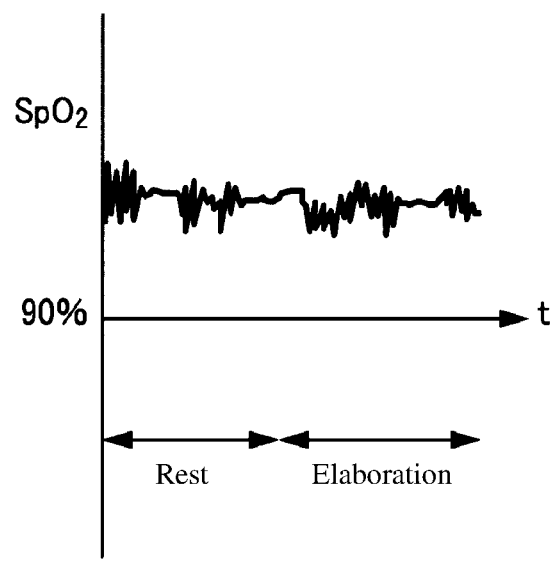

OXYGEN SUPPLY DEVICE AND METHOD FOR CONTROLLING SAME

CROSS REFERENCE TO RELATED APPLICATIONS

This application is a National Stage of International Application No. PCT/JP2018/010818 filed Mar. 19, 2018, claiming priority based on Japanese Patent Application No. 2017-069845 filed Mar. 31, 2017.

TECHNICAL FIELD

The present invention relates to an oxygen supply device used for oxygen therapy with inhalation of high concentration oxygen and a control method thereof.

BACKGROUND ART

An oxygen therapy is regarded as a therapy for chronic respiratory failure such as chronic obstructive pulmonary disease, pulmonary tuberculosis sequelae and pulmonary fibrosis and chronic respiratory disease, such as hypoxemia, caused by heart failure and other various diseases. The oxygen therapy aims to improve/prevent hypoxemia by raising oxygen partial pressure in arterial blood (PaO2) of patients through administration of high concentration oxygen gas.

A home oxygen therapy is a therapy in which a patient as a user of the oxygen supply device operates the device according to the prescription of the healthcare worker such as a physician, and receives the oxygen therapy at home. In the home oxygen therapy, the oxygen gas for inhalation is supplied from the oxygen supply device such as an oxygen concentration device and an oxygen cylinder described in PTL 1 or 2. Generally, an oxygen concentration device is used at home and a small and lightweight oxygen cylinder is often used outside home, such as going to hospital and shopping, for their convenience and ease of maintenance at use.

In the home oxygen therapy, it is desirable to prescribe the flow rate of the oxygen gas suitable for the state of each patient such as being at rest, elaboration, sleep as well as the disease and severity. For this purpose, it is under investigation to provide the oxygen supply device with a sensor measuring percutaneous arterial oxygen saturation (SpO2) as in PTL 1, and to set the flow rate of the oxygen gas based on the measured level of SpO2. Generally, it is thought to be desirable to keep a PaO2 level of a patient at 60 mmHg or more (a SpO2 level at 90% or more).

CITATION LIST

Patent Literature

[PTL 1] Japanese Unexamined Patent Application Publication No. 2001-309981
[PTL 2] Japanese Unexamined Patent Application Publication No. 2014-64772

SUMMARY OF INVENTION

Technical Problem

Chronic respiratory failure is classified into 2 types: type 1 respiratory failure, without hypercapnia (carbon dioxide partial pressure in arterial blood PaO2≤45 mmHg) and type 2 respiratory failure, with hypercapnia (carbon dioxide partial pressure in arterial blood PaO2>45 mmHg).

Generally, in the case of healthy subjects or patients with type 1 respiratory failure, the ventilation state is controlled by the CO2 ventilatory drive, and therefore increase in SpO2 level through the oxygen therapy hardly causes an abnormal change in the respiratory rate. On the contrary, in the case of patients with type 2 respiratory failure who are exposed routinely to the state of high carbon dioxide partial pressure in arterial blood (PaO2), not a few of the patients have the above CO2 ventilatory drive function attenuated. In this case, a ventilation state is controlled by the O2 ventilatory drive, therefore improvement of SpO2 through the oxygen therapy may cause the following abnormal respiratory condition: in the case of patients with the CO2 ventilatory drive function attenuated, an increase in the oxygen gas flow rate larger than required for raising the SpO2 level may terminate the O2 ventilatory drive and result in a sudden rise of the PaCO2 level. The sudden rise in the PaCO2 level may cause a clinical condition called CO2 narcosis, and lead to a serious risk such as disturbance of consciousness.

However, oxygen therapy is considered to give patients with type 2 respiratory failure a good prognosis, thus the CO2 narcosis is not a contraindication to the oxygen therapy. The oxygen therapy is desirably conducted with careful consideration of the CO2 narcosis risk.

The oxygen therapy with consideration of the CO2 narcosis risk requires to measure the PaCO2 level of the patient and control the PaCO2 level so as to avoid an excess level. However, it is presently difficult from the reasons of cost, reliability and the like to equip each oxygen supply device used for home oxygen therapy with a PaCO2 sensor and for each user receiving home oxygen therapy to receive oxygen therapy each time while measuring the PaCO2 level. The present invention is based on the above consideration, thus aims to provide an oxygen supply device that can detect a sign of the CO2 narcosis without requiring direct measurement of PaCO2 level, and a control method thereof.

Solution to Problem

The present invention includes the following embodiments of (1)-(12).

(1) An oxygen supply device supplying a user with an oxygen gas for inhalation, comprising: a first sensor unit acquiring information on percutaneous arterial oxygen saturation (SpO2) of the user, a second sensor unit acquiring information on vital signs that fluctuate in accordance with a rise in carbon dioxide partial pressure in arterial blood of the user, and a control unit controlling supply rate of the oxygen gas, and, under the controlled supply rate, judging a risk of an abnormal increase in the carbon dioxide partial pressure in arterial blood of the user, wherein in the case where a level of the percutaneous arterial oxygen saturation is equal to or larger than a first threshold and the information on vital signs is out of a predetermined range, the control unit judges the case as a sign of the abnormal increase in the carbon dioxide partial pressure in arterial blood of the user.

(2) The oxygen supply device according to (1), wherein the information on vital signs includes a respiratory frequency of the user, and in the case where a level of the percutaneous arterial oxygen saturation (SpO2) is equal to or larger than a first threshold and a value of the respiratory frequency is equal to or larger than a second threshold, the control unit judges the case as the sign.

(3) The oxygen supply device according to (1) or (2), wherein the oxygen supply device is an oxygen concentration device that concentrates oxygen in the air and supplies the oxygen gas using the concentrated oxygen gas.

(4) The oxygen supply device according to (1) or (2), wherein the oxygen supply device supplies the oxygen gas using a high-pressure oxygen gas filled in a cylinder.

(5) The oxygen supply device according to any one of (1) to (4), wherein the control unit controls the flow rate of the oxygen gas to zero or an initial set value when judging that the sign has appeared.

(6) The oxygen supply device according to any one of (1) to (5), wherein the control unit gives an alert when judging that the sign has appeared.

(7) The oxygen supply device according to any one of (1) to (6), wherein the first sensor unit is a pulse oximeter.

(8) The oxygen supply device according to any one of (1) to (7), wherein the control unit controls the flow rate of the oxygen gas based on the level of the percutaneous arterial oxygen saturation (SpO2).

(9) A control method for an oxygen supply device supplying a user with an oxygen gas for inhalation, comprising: a first step of acquiring information on percutaneous arterial oxygen saturation (SpO2) of the user, a second step of acquiring information on vital signs that fluctuate in accordance with a rise in carbon dioxide partial pressure in arterial blood of the user, a third step of judging a risk of an abnormal increase in the carbon dioxide partial pressure in arterial blood of the user, wherein in the case where the level of the percutaneous arterial oxygen saturation (SpO2) is equal to or larger than a first threshold, and the information on vital signs is out of a predetermined range, the third step judges the case as a sign of the abnormal increase in the carbon dioxide partial pressure in arterial blood of the user.

(10) The control method according to (9), wherein the information on vital signs includes a respiratory frequency of the user, and in the case where the level of the percutaneous arterial oxygen saturation (SpO2) is equal to or larger than a first threshold and the value of the respiratory frequency is equal to or larger than a second threshold, the third step judges the case as the sign.

(11) The control method according to (9) or (10), further comprising a fourth step of controlling the flow rate of the oxygen gas to zero or an initial set value when it is judged that the sign has appeared in the third step.

(12) The control method according to any one of (9) to (11), further comprising a fifth step of giving an alert when it is judged that the sign has appeared in the third step.

Advantageous Effects of Invention

In accordance with the present invention, an oxygen supply device and a control method thereof can be provided that can detect a sign of CO2 narcosis without requiring direct measurement of PaCO2 level.

BRIEF DESCRIPTION OF DRAWINGS

FIG. 1 is the schematic diagram illustrating the ventilatory responses to hypercapnia of a healthy subject/patient with type 1 respiratory failure and a patient with type 2 respiratory failure.

FIG. 2 is the flow diagram illustrating the control flow in the embodiment.

FIG. 3 shows the configuration of the oxygen concentration device.

FIG. 4a-FIG. 4b are diagrams illustrating the SpO2 feedback function.

DESCRIPTION OF EMBODIMENTS

Embodiments of the present invention are explained with reference to Figs.

Information on vital signs that fluctuate in accordance with a rise in carbon dioxide partial pressure in arterial blood includes respiration frequency, heart rate, pulse rate associated with heart rate, blood pressure, and the like.

Focusing on information on vital signs of respiratory frequency, the ventilatory response to carbon dioxide is generally as shown in FIG. 1 for a healthy subject/patient with type 1 respiratory failure both having normal ventilatory drive and a patient with type 2 respiratory failure. FIG. 1 is a schematic diagram illustrating the relation between carbon dioxide partial pressure in arterial blood (PaCO2) and respiratory frequency per minute (breath per minute: BPM) for a healthy subject/patient with type 1 respiratory failure and a patient with type 2 respiratory failure. The solid line and the dotted line each are for a healthy subject/patient with type 1 respiratory failure and a patient with type 2 respiratory failure, respectively.

In the case of a healthy subject, when PaCO2 level reaches a certain value or larger, the ventilatory function is stimulated and carbon dioxide is exhaled, thus BPM increases linearly (portion A in FIG. 1). In the case of a patient with type 2 respiratory failure, on the contrary, the response is generally slow to the increase in PaCO2 level, thus BPM begins to increase behind the case of a healthy subject (portion B in FIG. 1). In addition, a further increase in PaCO2 level causes respiratory acidosis accompanying attenuation of spontaneous respiration, thus BPM turns to decrease (portion C in FIG. 1). Continuation of the hypoventilation further raises PaCO2 level of the patient and increases the risk of CO2 narcosis.

The present embodiment of the oxygen supply device is for a user receiving home oxygen therapy, and has a first sensor unit measuring the percutaneous arterial oxygen saturation (SpO2) of the user and a second sensor unit measuring respiratory frequency per minute (BPM) of the user. For the judgment of an abnormal condition, when BPM increases while SpO2 level is equal to or larger than a fixed value, the oxygen supply device is controlled based on the judgement that the user is probably in the condition of portion B in FIG. 1 (the first sign of CO2 narcosis). Optionally, in addition, when BPM decreases while SpO2 level is equal to or larger than a fixed value, the oxygen supply device is controlled based on the judgement that the user is probably in the condition of portion C in FIG. 1 (the second sign of CO2 narcosis).

Although in the case mentioned above, the condition shifts from portion B to portion C in FIG. 1 with the increase in PaCO2 level, another case can be considered where the condition shifts directly to portion C in FIG. 1 with administration of high flow rate of oxygen to a patient at an acute phase. Even in the latter case, the present embodiment can catch the abnormal sign of the patient.

A control flow of the oxygen supply device executed by the control unit is shown in FIG. 2. After the oxygen supply device starts operation, the oxygen supply device supplies a patient with highly concentrated oxygen gas (e.g., 90% or more of oxygen concentration) using a nasal cannula (step S1). The first sensor unit measuring SpO2 level and the second sensor unit measuring BPM each measure the SpO2 level and the BPM value in a predetermined interval, respectively, and send the measured values to the control unit (step S2). The first sensor unit measuring the SpO2 level preferably uses a pulse oximeter, and the second sensor unit measuring the BPM can use any well-known sensor as long as the sensor can measure respiratory frequency.

The control unit compares a measured SpO2 level with a predetermined first threshold "a" (e.g., 90%) (step S3). When the measured SpO2 level is lower than the first threshold "a", the unit goes back to step S2 and continues to measure the SpO2 level and the BPM value while supplying the oxygen gas. When SpO2 level is equal to or larger than the first threshold "a", the unit proceeds to step S4, and checks a BPM value.

A second threshold "b" for BPM level is set beforehand. The second threshold "b" is set, as in FIG. 1, supposing a high PaCO2 level and an increasing BPM value of a patient with type 2 respiratory failure. As generally known, a criterion of a sudden change in the sign of patients with type 2 respiratory failure is considered as a case where BPM exceeds a value around 30, and thus the second threshold "b" is set at, for example, 30 of BPM. The control unit compares a measured BPM value with the predetermined second threshold "b" (step S4). When the measured BPM value is lower than the second threshold "b", the control unit goes back to step S2 and continues to measure SpO2 level and BPM value while supplying the oxygen gas. On the contrary, when the measured BPM value is equal to or larger than the second threshold "b", the control unit judges that the user shows a sign of the abnormal increase in the carbon dioxide partial pressure in arterial blood (step S5).

The condition where the SpO2 level is equal to or larger than the first threshold "a" and BPM value has increased to the second threshold "b" or larger, can be considered to be the condition of portion B of FIG. 1 where an increase in PaCO2 caused by insufficient exhalation of CO2 stimulates BPM to increase, namely occurrence of the first sign of CO2 narcosis. Thus the control unit judges the condition as an abnormal sign (step S5), and immediately sets the flow rate of the oxygen gas to zero (step S6).

Although, in the control flow of FIG. 2, the flow rate of the oxygen gas is turned to zero and supply of the oxygen gas is stopped in step S6, a procedure of the step after judging the abnormal sign is not limited to this. The procedure can be, for example, the following: an initial flow rate is predetermined to a low flow rate unlikely to cause CO2 narcosis; upon judging the abnormal sign in step 5; the control unit turns flow rate of the oxygen gas to the initial flow rate in step S6; and supply of the oxygen gas is continued. The step S6 can be followed by an additional step where the oxygen supply device gives an alert.

Although, in step S4, a BPM upper limit is provided as a second threshold "b" and the case where the BPM value is equal to or larger than the second threshold "b" is judged as an abnormal sign, another judgement can be done by adding a BPM lower limit (e.g., BPM of 10) as a third threshold "c". Optionally, when, in step S4, a BPM value is equal to or larger than the second threshold "b" or equal to or less than the third threshold "c", the control proceeds to step S5 and judges that an abnormal sign has appeared. The condition where a BPM value is equal to or less than the third threshold "c" can be considered to be a decrease in BPM corresponding to portion C of FIG. 1, and thus is judged as an abnormal sign, namely high possibility of the second sign of CO2 narcosis. The BPM lower limit as third threshold "c" as well as the BPM upper limit as second threshold "b" can enhance reliability of detecting the sign of CO2 narcosis. Another case can be considered that the condition shifts directly to portion C in FIG. 1 at an administration of a high flow rate of oxygen to a patient in an acute phase. Even in this case, the present example can catch the abnormal sign of the patient.

EXAMPLES

The configuration of the oxygen concentration device is represented in FIG. 3 as an example of the oxygen supply equipment of the present invention. The oxygen concentration device is mainly used for home oxygen therapy as explained above. The oxygen concentration device is a device that isolates nitrogen contained in the air and supplies high concentration oxygen (oxygen-enriched gas) as an oxygen gas for inhalation. In FIG. 3, the solid line and the dotted line connecting each component represent a gas flow path and a path of electric signal such as control signal, respectively. Note that, an oxygen supply device of the present invention is not limited to an oxygen concentration device, and may be an oxygen supply device that supplies an oxygen gas for inhalation using high-pressure oxygen gas filled in a cylinder.

In the oxygen concentration device of the example, an SpO2 level of the oxygen concentration device user receiving home oxygen therapy is measured using pulse oximeter 2 (first sensor unit), and control unit 103 is equipped with a feedback function for controlling an oxygen gas flow rate so as to adjust the SpO2 level to an SpO2 set point (e.g., 90%-94%) prescribed by a physician and the like. Use of the SpO2 feedback function enables the oxygen concentration device to supply oxygen gas at a more suitable flow rate depending on each user's state such as being at rest, elaboration and sleep, leading to the expectation of enhancing an effect of the home oxygen therapy. In addition, the safety also can be enhanced by detecting a sign of CO2 narcosis as described above.

In the oxygen concentration device, main body 1 contains compressor 102 supplying compressed air, adsorption cylinder 107 filled with an adsorbent selectively adsorbing nitrogen rather than oxygen, switching valve 105 switching the sequence such as adsorption step, desorption step and the like, control valve 104 increasing or decreasing a flow rate of the concentrated oxygen gas, and the like and control unit 103 controlling these components. Control unit 103 is composed of, for example, CPU (central processing unit).

The oxygen gas is concentrated by main body 1, is adjusted its flow rate by control valve 104, and is supplied to a home oxygen therapy user via cannula 4. The flow rate of the oxygen gas is adjusted to a set point, for example, between 0.25 L/min and 5.00 L/min by a control from control unit 103 to control valve 104. Pulse oximeter 2 as a first sensor unit is attached to the fingertip and the like of the user, and measures SpO2 level and sends it to control unit 103. Second sensor unit acquiring information on vital signs that fluctuate in accordance with a rise in carbon dioxide partial pressure in arterial blood of the user is BPM sensor 3, measures a BPM value of the user and sends it to control unit 103.

The raw material air is taken into main body 1 through the air inlet equipped with air inlet filter 101 that removes foreign substances such as dusts. At this time, about 21% of oxygen gas, about 77% of nitrogen gas, 0.8% of argon gas, and 1.2% of carbon dioxide and other gases are contained in the air. The oxygen concentration device concentrates only the oxygen gas necessary for respiration gas and takes it out.

The raw material air taken into main body 1 is compressed by compressor 102, transferred to adsorption cylinders 107 filled with an adsorbent made of zeolite and the like that selectively adsorbs nitrogen molecules. Control unit 103, by operating switching valve 105, sequentially switches the target adsorption cylinder, supplies the raw material air to the cylinder and selectively adsorbs and removes the nitrogen gas that occupies about 77% of the raw material air in the adsorption cylinders 107.

Adsorption cylinders 107 can adopt a well-known configuration such as multiple-cylinder type having three or more cylinders as well as single-cylinder and double-cylinder types, and for the purpose of continuous and efficient manufacture of oxygen-enriched gas from the raw material air, adsorption cylinders 107 preferably adopt a double-cylinder type or a multiple-cylinder type. In the case of a pressure swing adsorption type (PSA type) oxygen concentration device of a double-cylinder type, while one adsorption cylinder (cylinder A) executes an adsorption step, the other cylinder (cylinder B) executes a desorption step, and switching valve 105 is controlled so that steps of both cylinders are sequentially switched between adsorption step and desorption step each in an opposite phase, and thus oxygen is manufactured continuously.

Compressor 102 adopts a compressor having only a compression function or compression and vacuum functions such as a two-head swing-type air compressor, and in some cases, rotation-type air compressors including screw type, rotary type, scroll type and the like. A power supply for a motor driving compressor 102 may be AC or DC.

The nitrogen gas in the air is adsorbed on the adsorbent in adsorption cylinder 107 at a compressed state, and the oxygen-enriched gas mainly composed of the unadsorbed oxygen is taken out of adsorption cylinder 107. The oxygen-enriched gas taken out flows into product tank 106 through check valve 108 equipped to prevent backflow into adsorption cylinder 107, and is accumulated in product tank 106. The oxygen-enriched gas accumulated in product tank 106 is an oxygen gas with high concentration of, for example, 95%.

The oxygen gas is adjusted to a flow rate prescribed by a physician and the like by controlling control valve 104, and supplied to a patient through cannula 4. Oxygen concentration/flow rate sensor 110 feeds back values of the flow rate and the oxygen concentration of the supplied oxygen gas to control unit 103, enabling the oxygen concentration device to control manufacture and supply of the oxygen gas.

The oxygen concentration device of the example, in order to detect a sign of CO2 narcosis, measures an SpO2 level and a BPM value at a predetermined interval using pulse oximeter 2 and BPM sensor 3, and sends the measured values to control unit 103. Control unit 103 judges an abnormal sign according to the flow in FIG. 2 and when judging that the sign of CO2 narcosis has appeared, controls control valve 104 to stop supply of the oxygen gas. Then it controls compressor 102 and switching valve 105 to stop manufacture of the oxygen gas. At the same time, control unit 103 gives an alert to inform the user that the supply of the oxygen gas has stopped.

Control unit 103 judges the sign of CO2 narcosis from the SpO2 level and the BPM value. Therefore, control unit 103 can control the oxygen concentrator while predicting the risk of CO2 narcosis without providing the oxygen concentration device with a sensor for PaCO2. The judgement of the sign of CO2 narcosis by control unit 103 of the oxygen concentration device can further enhance safety of the user receiving home oxygen therapy.

When a user activates an SpO2 feedback function of the oxygen concentration device, control unit 103 controls control valve 104 to adjust the oxygen gas flow rate so that the SpO2 level measured by pulse oximeter 2 is in the range (e.g., 90%-94%) prescribed by a healthcare worker such as a physician and the like.

In the case where an oxygen concentration device has a fixed flow rate for oxygen gas supply, the user is required to operate the oxygen concentration device and change the oxygen gas flow rate depending on patient's own state, otherwise there may happen deficiency or excess of the oxygen gas. For example, as shown in FIG. 4(a), when the user shifts from rest to elaboration, consumption of oxygen increases, and the SpO2 level lowers. Thus, unless the oxygen gas flow rate is changed from prescription at rest to at elaboration, the user feels discomfort like suffocation and the like.

On the other hand, when the SpO2 feedback function of the oxygen concentration device is activated, control unit 103 controls the oxygen gas flow rate based on the SpO2 level measured with pulse oximeter 2. Therefore, as shown in FIG. 4(b), when a user shifts from rest to elaboration and oxygen consumption increases, control unit 103 increases the oxygen gas flow rate to prevent decrease in the SpO2 level. The increase in the oxygen gas flow rate keeps the SpO2 level constant, and thus can prevent the user from feeling discomfort such as suffocation and the like. The oxygen concentration device supplies the oxygen gas while adjusting the flow rate so that the SpO2 level is in the prescribed range, and thus it can be expected to enhance the effect of home oxygen therapy.

In the oxygen concentration device of the example, control unit 103 executes the control flow in FIG. 2 even under the activation of the SpO2 feedback function. The SpO2 feedback function allows control unit 103 to increase or decrease the oxygen gas flow rate so that the SpO2 level is in the prescribed range. Even when the oxygen gas flow rate increases, control unit 103 monitors a sign of CO2 narcosis from the SpO2 level and the BPM value according to the flow in FIG. 2, and on the judgement of abnormality, stops the SpO2 feedback function, and stops the supply of the oxygen gas or changes the supply to a predetermined initial flow rate that is a low flow rate unlikely to cause CO2 narcosis. Therefore, the oxygen concentration device can further enhance safety of the user receiving home oxygen therapy.

Though a preferred embodiment of the present invention was explained in detail as above, the present invention is not limited to the embodiment mentioned above, and various kinds of variation and modification are possible within the contents of the present invention described in the scope of claims.

INDUSTRIAL APPLICABILITY

The oxygen supply device of the present invention enables early detection of a sign of CO2 narcosis, and therefore can further enhance safety of the user receiving home oxygen therapy using the oxygen concentration device.

REFERENCE SIGNS LIST

1. Main body
2. Pulse oximeter (first sensor unit)
3. BPM sensor (second sensor unit)
4. Cannula 101. Air inlet filter
102. Compressor
103. Control unit
104. Control valve
105. Switching valve
106. Product tank
107. Adsorption cylinder
108. Check valve
109. Pressure regulating valve
110. Oxygen concentration/flow rate sensor

The invention claimed is:

1. An oxygen supply device supplying a user with an oxygen gas for inhalation, comprising:
   a first sensor unit configured to sense information on percutaneous arterial oxygen saturation (SpO2) of the user,
   a second sensor unit configured to sense information on vital signs that fluctuate in accordance with a rise in carbon dioxide concentration in blood of the user, the information on vital signs indicating a respiratory frequency, in breaths per minute (BPM), of the user,
   a control unit configured to control a supply rate of the oxygen gas, and, under the controlled supply rate, judging a risk of an abnormal increase in the carbon dioxide partial pressure in arterial blood of the user,
   wherein the control unit is further configured to:
      control a supply of the oxygen gas;
      check and determine whether the level of percutaneous arterial oxygen saturation is equal to or larger than a first threshold;
      in response to determining that the level of percutaneous arterial oxygen saturation is equal to or larger than the first threshold, check and determine whether the information on the vital signs is out of a predetermined range;
      in response to determining that the information on the vital signs is out of the predetermined range, judge the level of percutaneous arterial oxygen saturation and the information on the vital signs as indicating a sign of the abnormal increase in the carbon dioxide partial pressure in arterial blood of the use; and
      control the supply of the oxygen gas based on whether the level of percutaneous arterial oxygen saturation and the information on the vital signs is judged as indicating the sign of the abnormal increase in the carbon dioxide partial pressure in arterial blood of the user.

2. The oxygen supply device according to claim 1, wherein
   in the case where a level of the percutaneous arterial oxygen saturation (SpO2) is equal to or larger than a first threshold and a level of the respiratory frequency is equal to or larger than a second threshold, the control unit judges the case as the sign.

3. The oxygen supply device according to claim 1, wherein the oxygen supply device is an oxygen concentration device that concentrates oxygen in the air and supplies the oxygen gas using the concentrated oxygen gas.

4. The oxygen supply device according to claim 1, wherein the oxygen supply device supplies the oxygen gas using a high-pressure oxygen gas filled in a cylinder.

5. The oxygen supply device according to claim 1, wherein the control unit controls the flow rate of the oxygen gas to zero or an initial set value when judging that the sign has appeared.

6. The oxygen supply device according to claim 1, wherein the control unit gives an alert when judging that the sign has appeared.

7. The oxygen supply device according to claim 1, wherein the first sensor unit is a pulse oximeter.

8. The oxygen supply device according to claim 1, wherein the control unit controls the flow rate of the oxygen gas based on the level of the percutaneous arterial oxygen saturation (SpO2).

9. A control method for an oxygen supply device supplying a user with an oxygen gas for inhalation, comprising:
   a first step of sensing information on percutaneous arterial oxygen saturation (SpO2) of the user,
   a second step of sensing information on vital signs that fluctuate in accordance with a rise in carbon dioxide partial pressure in arterial blood of the user,
   a third step of judging, using a control unit, a risk of an abnormal increase in the carbon dioxide partial pressure in arterial blood of the user,
   wherein the control method, using the control unit, further comprises:
      controlling a supply of the oxygen gas;
      checking and determining whether the level of percutaneous arterial oxygen saturation is equal to or larger than a first threshold;
      in response to determining that the level of percutaneous arterial oxygen saturation is equal to or lamer than the first threshold, checking and determining whether the information on the vital sins is out of a predetermined range;
      in response to determining that the information on the vital sins is out of the predetermined range, judging the level of percutaneous arterial oxygen saturation and the information on the vital sins as indicating a sign of the abnormal increase in the carbon dioxide partial pressure in arterial blood of the use; and
      controlling a supply of the oxygen gas based on whether the level of percutaneous arterial oxygen saturation and the information on the vital sins is judged as indicating the sign of the abnormal increase in the carbon dioxide partial pressure in arterial blood of the user.

10. The control method for an oxygen supply device according to claim 9, wherein
    in the case where the level of the percutaneous arterial oxygen saturation (SpO2) is equal to or larger than a first threshold and the value of the respiratory frequency is equal to or larger than a second threshold, the third step judges the case as the sign.

11. The control method according to claim 9, further comprising a fourth step of controlling the flow rate of the oxygen gas to zero or an initial set value when it is judged that the sign has appeared in the third step.

12. The control method according to claim 9, further comprising a fifth step of giving an alert when it is judged that the sign has appeared in the third step.

13. The oxygen supply device according to claim 2, wherein the second threshold is 30 BPM.

14. The oxygen supply device according to claim 1, wherein the sign of the abnormal increase indicates carbon dioxide narcosis.

15. The oxygen supply device according to claim 1, wherein controlling the supply of the oxygen gas comprises stopping the supply of the oxygen gas to the user.

* * * * *